United States Patent [19]

Sibalis

[11] 4,211,225
[45] Jul. 8, 1980

[54] TAMPON WITH A COLLAPSIBLE AND INVERTIBLE SHROUD

[76] Inventor: Dan Sibalis, c/o Link Controls, Inc., 2111 Lakeland Ave., Ronkonkoma, N.Y. 11779

[21] Appl. No.: 925,938

[22] Filed: Jul. 19, 1978

[51] Int. Cl.² ............................................. A61F 13/20
[52] U.S. Cl. ............................................................. 128/285
[58] Field of Search .......... 128/263, 270, 285, 759–760

[56] References Cited

U.S. PATENT DOCUMENTS

| | | | |
|---|---|---|---|
| 3,814,099 | 6/1974 | Kobler | 128/285 |
| 4,018,225 | 4/1977 | Elmi | 128/285 |

*Primary Examiner*—Robert W. Michell
*Assistant Examiner*—C. F. Rosenbaum

[57] ABSTRACT

A tampon designed for catamenial or medical use which includes a collapsible and invertible shroud (13) affixed to the front or inserted end (17) of the main tampon body (12). The shroud has an inner layer (15), adjacent to the main tampon body, fabricated from a smoothly gliding, yet permeable material which allows the main tampon body to slide from the shroud upon withdrawal. The shroud is also configured to invert behind the main tampon body during withdrawal. The collapsed and inverted shroud is significantly smaller than the main tampon body and barely contacts the surrounding body tissue, thereby eliminating withdrawal irritation.

5 Claims, 8 Drawing Figures

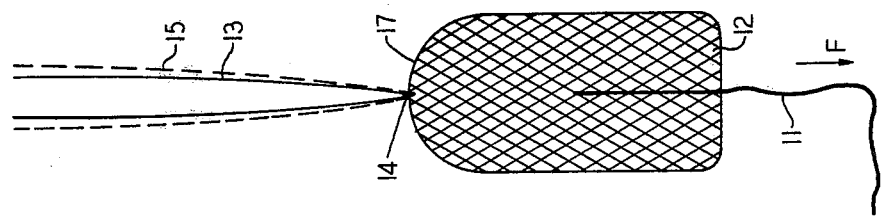
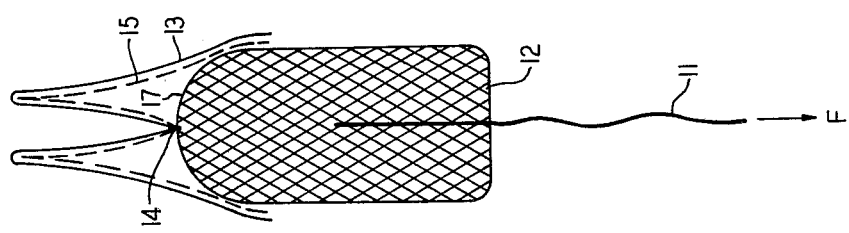
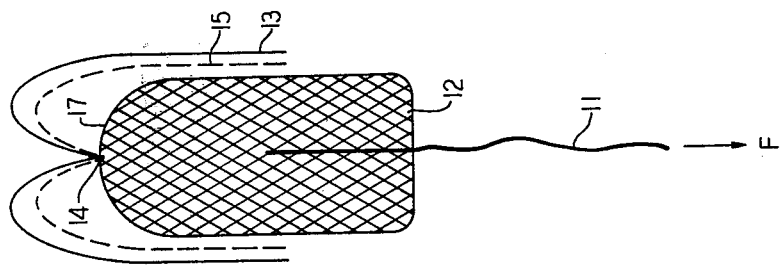

TAMPON WITH A COLLAPSIBLE AND INVERTIBLE SHROUD

TECHNICAL FIELD

The present invention relates to an absorbent tampon for catamenial or medical use and, in particular, to a tampon having a collapsible and invertible shroud configured to lessen the discomfort associated with tampon withdrawal.

BACKGROUND ART

Aside from their commonly known use as an article of feminine hygiene, tampons are used in a wide variety of medical applications. For example, after an operative procedure, tampons have been employed as a surgical dressing and in addition, German Patent No. 1,018,156 issued to Dr. med Hermann Casser, issued May 8, 1958 discloses the use of an adapted tampon for positioning a suppository in the human body.

These and other uses have stimulated development of tampon materials with improved absorbency, as well as tampon modifications to make insertion easier. In U.S. Pat. No. 3,814,099, issued to Paul Kobler on June 4, 1974, a tampon having a moisture repellent foil extending therefrom to cover a person's hand during insertion is disclosed. This foil folds back from the rear end of the tampon to provide a protective cover for the hand.

Despite these advances, tampons are still disfavored because of the discomfort during tampon withdrawal. For many women, the extraction of a catamenial tampon is uncomfortable and irritating due to the often dry state of the vaginal walls. This dryness produces a high degree of adhesion between the tampon and vaginal walls, thereby causing discomfort on withdrawal. Similarly, in surgical applications, tampon removal irritates the surrounding tender, healing body tissue.

SUMMARY OF THE INVENTION

According to the present invention, the discomfort and irritation on tampon withdrawal is substantially eliminated by the use of a tampon with a collapsible shroud of permeable material affixed to the front or inserted end of the main tampon body. The shroud has an inner layer, adjacent to the main tampon body, fabricated from a smoothly gliding, yet permeable material. This low friction layer allows the main tampon body to slide from the shroud upon withdrawal.

As this sliding occurs in withdrawal, the shroud is also configured to readily collapse and invert behind the main tampon body. Upon inversion and collapse the shroud becomes significantly smaller in diameter than the main tampon body and thereby barely contacts the surrounding body tissue. This invert/ collapse feature may be achieved by a variety of techniques. In one of many possible schemes, the outer shroud folds up in an umbrella-like fashion. In still another embodiment, the shroud may be configured to telescope behind the main tampon body. As a result of these features, the irritating sliding of the tampon against sensitive human tissue is eliminated.

Another advantage of the present invention is its ready adaption to conventional tampon configurations. Moreover, presently available material compositions allow the fabrication of a low friction, smoothly gliding inner liner with a range of coefficients of sliding friction. Particular coefficients of friction can be selected to meet a range of human sensitivities. It will, of course, be understood that for any particular coefficient selected, the collapsing and inversion features, discussed supra, will not operate until the particular friction force is overcome. Therefore, if the surrounding vaginal walls are moist and withdrawal irritation will not be a problem, the present invention functions as a conventional tampon. Alternatively, dry vaginal walls serve to activate the inventive concepts and advantageously permit tampon withdrawal without the irritation inherent in prior art tampons. In summary, the features of this invention are self-actuating and operate only when required. Therefore, the discussed advantages of the present invention can be utilized in any tampon application.

BRIEF DESCRIPTION OF THE DRAWINGS

FIGS. 1 through 6 show a progression of cross-sectional views of either FIGS. 7 and 8 schematically represented.

FIG. 1 shows the tampon after insertion;

FIG. 2 depicts the expanded, saturated tampon prior to withdrawal;

FIG. 3 illustrates the tampon upon initial withdrawal;

FIG. 4 illustrates the tampon during withdrawal;

FIG. 5 depicts the further extracted tampon;

FIG. 6 shows a tampon with the shroud fully collapsed and inverted;

DETAILED DESCRIPTION

Figure 1:
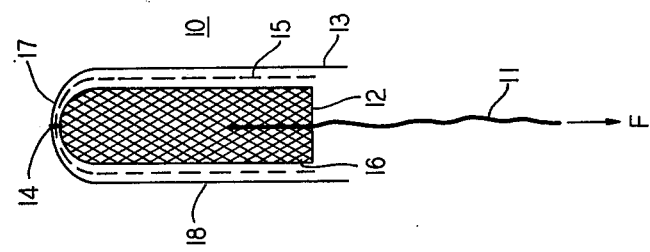

Illustrated in FIG. 1 is tampon 10 having a withdrawal cord 11 permanently affixed to the main tampon body 12. Surrounding the main tampon body 12 is shroud 13 also permanently affixed to main body 12 at point 14 on the front or inserted end 17 of tampon 10. Disposed between shroud 13 and main body 12 is a smoothly gliding, yet permeable layer 15. The sliding friction between layer 15 and the external surface 16, of main body 12, is configured to be less than the sliding friction between the external surface 18, of outer shroud 13, and the surrounding body tissue. This relationship permits the extraction of main body 12 first, followed by the collapse and inversion of outer shroud 13 behind main body 12, when withdrawal force F is applied to cord 11.

Figure 2:
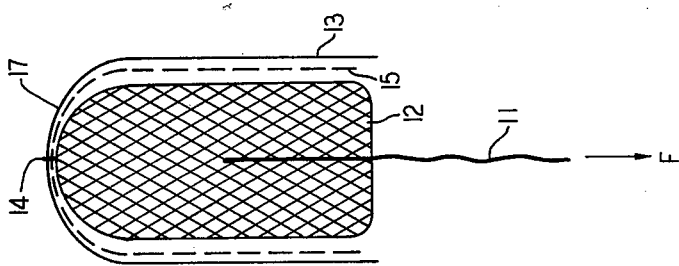

As shown, smoothly gliding layer 15 is separate and distinct from main body 12. Layer 15, however, can be advantageously fabricated as an integral part of outer shroud 13 by a variety of techniques. One such technique is to disperse a smooth material, such as nylon or polyprophylene, into a woven permeable material. Alternatively, layer 15 can be fabricated, in a similar fashion, as an integral part of main body 12. With this alternative, the friction between shroud 13 and the composite of main body 12 and layer 15 would obviously have to be less than the friction between external surface 18 and the surrounding body tissue. FIG. 2 depicts the same tampon of FIG. 1 in an expanded state due to the absorption of body fluids.

Figure 3:
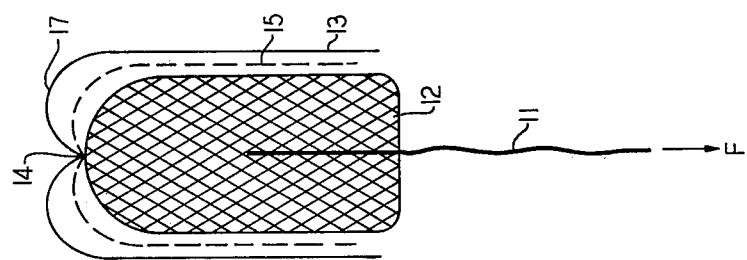

The initial withdrawal of the tampon is illustrated in FIG. 3. At this stage, responsive to force F, main body 12 has begun to slide relative to layer 15 and shroud 13.

Layer 15 and shroud 13, due to the higher frictional forces discussed supra, have also separated from inserted end 17 of main body 12, except at the point of affixation 14. As the application of force F continues this separation increases, as shown in FIG. 4. It should also be noted that, as illustrated in FIG. 4, both layer 15 and shroud 13 have begun to invert and collapse behind main body 12. FIG. 5 illustrates the nearly complete collapse of shroud 13 and layer 15 as main body 12 is further withdrawn from a body cavity. A slight additional force F withdraws layer 15 and shroud 13 as well. Upon complete withdrawal, the tampon appears as shown in FIG. 5 and/or FIG. 6, wherein FIG. 6 illustrates shroud 13 and layer 15 fully inverted and collapsed.

Figure 7:
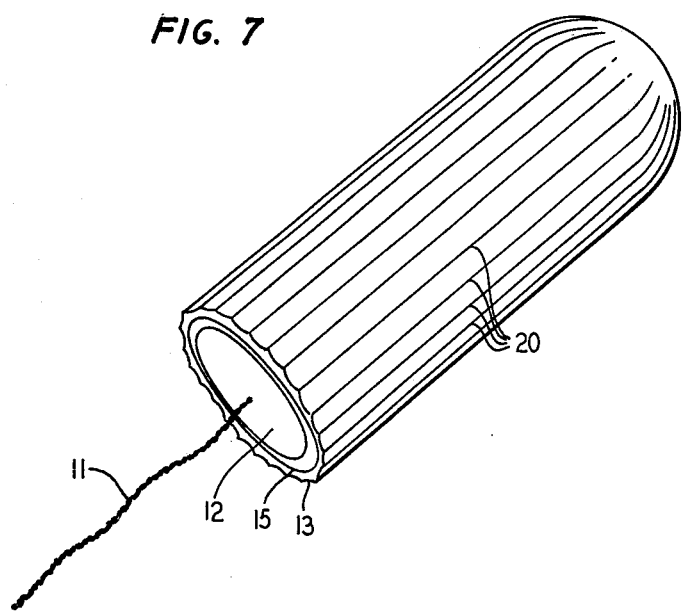
FIG. 7 illustrates a perspective view of one tampon embodiment with a conventional withdrawal cord having an outer shroud configured to fold up umbrella-like upon withdrawal.
Figure 8:
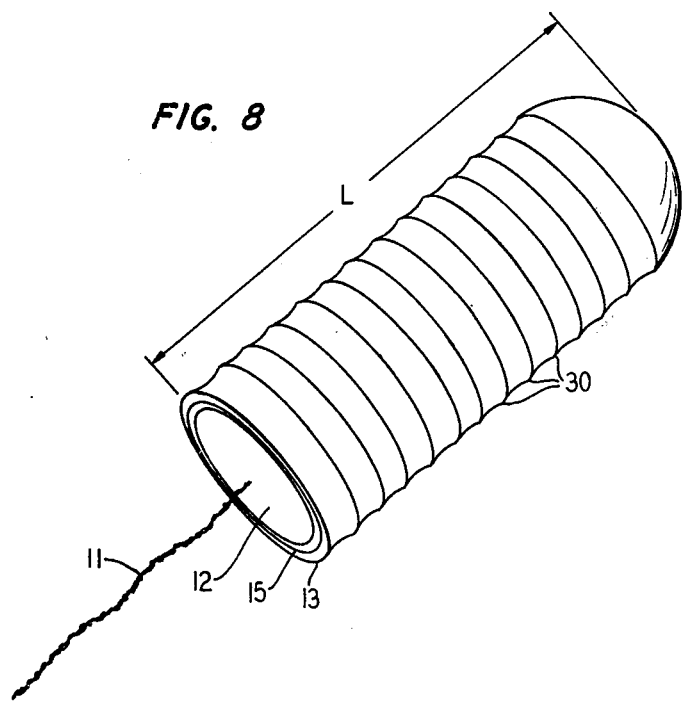
FIG. 8 illustrates another tampon embodiment where the outer shroud is designed to telescope behind the main tampon body.

Finally, FIGS. 7 and 8 show two embodiments of the invention configured to expedite the collapse and inversion of shroud 13 and layer 15. In FIG. 7, both these elements are slightly creased longitudinally 20 to permit their umbrella-like collapse. Alternatively, in FIG. 8, a plurality of circular creases 30 are spaced along the length L of shroud 13 and layer 15 to enhance the telescoping of shroud 13 and layer 15.

What is claimed is:

1. A tampon having a main body (12) and a withdrawal cord (11) affixed thereto, characterized in that said tampon further includes a collapsible and invertible shroud (13) affixed to said main body opposite said withdrawal cord and a smoothly gliding layer (15) included between said main body and said shroud, said layer (15) being configured so that the frictional forces between said main body and said layer are less than frictional forces between said shroud and the surrounding body tissue, to cause said main body to slide out from said shroud on withdrawal, progressively inverting and collapsing said shroud.

2. The tampon of claim 1 further characterized in that said shroud (13) is precreased circumferencially (30) so as to facilitate the collapse and inversion of said shroud upon withdrawal.

3. The tampon of claim 1 further characterized in that said shroud (13) is performed with a plurality of longitudinal creases (20) so as to facilitate the collapse and inversion of said shroud upon withdrawal.

4. The tampon of claim 1, characterized in that said smoothly gliding layer (15) is formed as an integral part of said main body (12).

5. The tampon of claim 1, characterized in that said smoothly gliding layer (15) is formed as an integral part of said shroud (13).

* * * * *